United States Patent [19]

Shwab

[11] Patent Number: 5,069,673
[45] Date of Patent: Dec. 3, 1991

[54] CATHETER WITH DOUBLE STEP-DOWN BORE

[75] Inventor: Jacqueline A. Shwab, Miami, Fla.

[73] Assignee: Cordis Corporation, Miami Lakes, Fla.

[21] Appl. No.: 475,938

[22] Filed: Feb. 7, 1989

[51] Int. Cl.⁵ .............................................. A61M 25/00
[52] U.S. Cl. ..................................... 604/280; 604/281; 604/282
[58] Field of Search ........................ 604/264, 280–282; 128/656, 658

[56] References Cited

U.S. PATENT DOCUMENTS

| | | | |
|---|---|---|---|
| 3,416,531 | 12/1968 | Edwards | 604/282 |
| 4,573,476 | 3/1986 | Ruiz | 128/658 |
| 4,639,252 | 1/1987 | Kelly et al. | 604/282 |
| 4,747,840 | 5/1988 | Ladika | 604/281 |
| 4,863,441 | 10/1989 | Lindsay et al. | 604/280 |

FOREIGN PATENT DOCUMENTS 2119261  8/1972  France ............................. 604/280

Primary Examiner—John D. Yasko
Assistant Examiner—T. Gutowski
Attorney, Agent, or Firm—Gerstman & Ellis Ltd.

[57] ABSTRACT

A catheter defines a flexible tubular body and a tubular tip carrier at the distal end of the body. At last the majority of the tubular body defines a first bore portion having a first meter. The catheter defines side holes adjacent the distal end, with the catheter defining a second bore portion distal to the side holes having a second diameter which is less than the first diameter. The catheter also defines an intermediate, tubular portion between the first and second bore portions, the intermediate portion having a third bore diameter that is less than the first diameter and greater than the second diameter. The intermediate portion also defines a thicker catheter wall than the catheter wall defining the first bore portion.

15 Claims, 1 Drawing Sheet

CATHETER WITH DOUBLE STEP-DOWN BORE

BACKGROUND OF THE INVENTION

Angiographic catheters are currently used in a variety of clinical procedures in which a fluid, particularly x-ray contrast media, is injected through the catheter into a blood vessel of the body leading to the heart, for use in flush studies and ventriculograms. To accomplish this, angiographic catheters are frequently threaded through the aorta and the heart itself to pass through a mitral valve for x-ray imaging of a heart ventricle or the like.

Many designs of angiographic catheters are known. However, typically, the currently preferred designs of angiographic catheters for flush studies or ventriculograms are so-called "pigtail" catheters, in which the distal tip of the catheter defines a loop, which facilitates the entry of the distal tip of the catheter through the mitral valve without causing any damage. Straight catheters are used for flush studies also.

Also, as shown for example in Ruiz U.S. Pat. No. 4,573,476, the distal end of an angiographic catheter may define side holes for the lateral outflow of x-ray contrast fluid or the like, along with a longitudinal distal exit for the catheter lumen, so that contrast fluid is also delivered out of the distal end of the catheter in longitudinal manner. The lumen of the catheter which is distal from the side holes may be of reduced diameter in order to direct a higher percentage of contrast fluid flow out of the lateral apertures, so that there is less direct forward flow of such fluid out of the distal tip.

Additionally, some commercially available pigtail-type angiographic catheters define a braided metal strand tubular reinforcing member positioned within the catheter wall along the majority of its length. However, this braided tubing is absent at the distal tip area where the side holes reside, and also in the pigtail area distal to the side holes.

Disadvantages have resulted in the manufacture of such catheters in that, while it is desirable to keep the catheter wall thickness to a minimum throughout its length, the braided metal strand reinforcing sleeve should be completely buried within the catheter wall and not exposed at either the inner or outer surfaces. Difficulties have arisen in keeping the braided metal sleeve so completely embedded, when a tubular distal tip is heat sealed to a separately formed portion of the catheter that carries the woven metal sleeve. Additionally, complaints have arisen in some currently available angiographic catheters of this type from surgeons who have reported that in clinical use, as they have attempted to put the pigtail tip through the mitral valve, the distal tip adjacent the junction between the tip and the rest of the catheter sometimes buckles. This is quite undesirable.

In accordance with this invention, an improved catheter is provided which may be used as an angiographic catheter, and which reduces or eliminates the manufacturing problem and the problem of clinical use described above. At the same time, the catheter can be made of a design which is otherwise substantially equivalent to the currently preferred angiographic catheters, to achieve the advantages that are presently obtained by such catheters, while avoiding the above-described limitations.

DESCRIPTION OF THE INVENTION

In accordance with this invention a catheter is provided which defines a flexible, tubular body having a bore extending the length thereof, and a tubular tip carried at the distal end of such body. At least the majority of the tubular body defines a first bore portion having a first diameter. The catheter defines side holes adjacent the distal end of the body and communicating with the bore, the side holes occupying a portion of the tubular tip.

The catheter also defines a second bore portion which is distal to the side holes, the second bore portion having a second diameter which is less than the first diameter.

The catheter also defines an intermediate bore portion between the first and second bore portions, which intermediate portion defines the side holes, and a third bore diameter that is less than the first diameter and greater than the second diameter. Also, the intermediate portion defines a thicker catheter wall than the catheter wall which defines the first bore portion. Thus, the catheter of this invention defines at least three different bore diameters, with the second and third bore diameters being respectively defined by the second bore portion and the intermediate bore portion which are each, in turn, typically defined in a tubular tip which is distal to the body, which body defines the first bore portion. These respective bore portions communicate with each other, and may be separated by stepped, bore reducing areas, to provide a double step-down bore, in contrast with the single step-down bore provided, for example, by the Ruiz patent cited above.

The flexible, tubular body of the catheter may be joined to the tubular tip at a bore-reducing junction area between the first bore portion and the intermediate portion. A second bore-reducing area may separate the intermediate and second bore portions.

While straight catheters may be used, it is currently preferred for the catheter part which defines the second bore portion to comprise a pigtail tip, typically at the catheter distal end and typically defining an almost complete loop. The bore of the catheter extends through the distal end thereof and, since the catheter can be flexible, the pigtail tip can be straightened out by the exertion of an internal force from a guide wire, or externally by the vascular system of a patient, as needed and desired.

Because the intermediate portion described above defines a thicker catheter wall and a smaller bore than the catheter wall defining the first bore portion, the process of heat-fusing a tubular tip to a catheter body which carries an embedded, braided reinforcement sleeve is rendered substantially easier, so that such a fusion step can take place with a significant reduction in the number of defective units made, in which a piece of the braided sleeve is exposed to the interior or the exterior surfaces of the catheter. Additionally, the thicker wall of the intermediate portion, which may define a plurality of side ports, provides a structure which has greater resistance against buckling or collapsing, even though it is not supported by a braided sleeve. Such heat fusing is performed on catheter components made of known thermoplastic materials.

The second reduction in bore size, from the intermediate portion to the second bore portion that defines the pigtail tip, provides further advantages to the catheter in that the amount of x-ray contrast fluid or the like which is expelled forwardly is reduced by the reduced-sized bore, while the expulsion of such fluids out of the lateral ports is increased, this being a situation which is often deemed clinically desirable.

Thus, a catheter is provided which exhibits the desirable clinical characteristics of the current best angiographic catheters, but the catheters of this invention are more easily manufactured, with a lower percentage of defective product. Also, the catheters perform better on a clinical basis, in that the buckling problem described above is reduced or eliminated.

DESCRIPTION OF SPECIFIC EMBODIMENT

Figure 1:
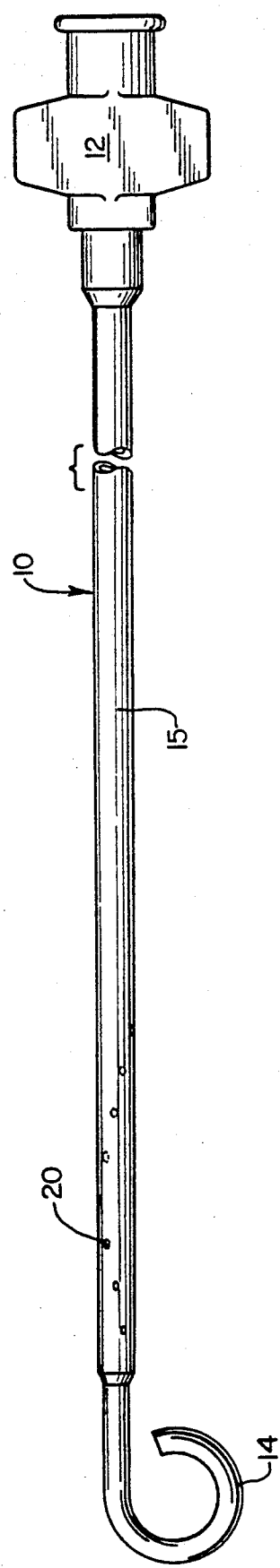
FIG. 1 is a plan view of a pigtail-type angiographic catheter made in accordance with this invention.
Figure 2:
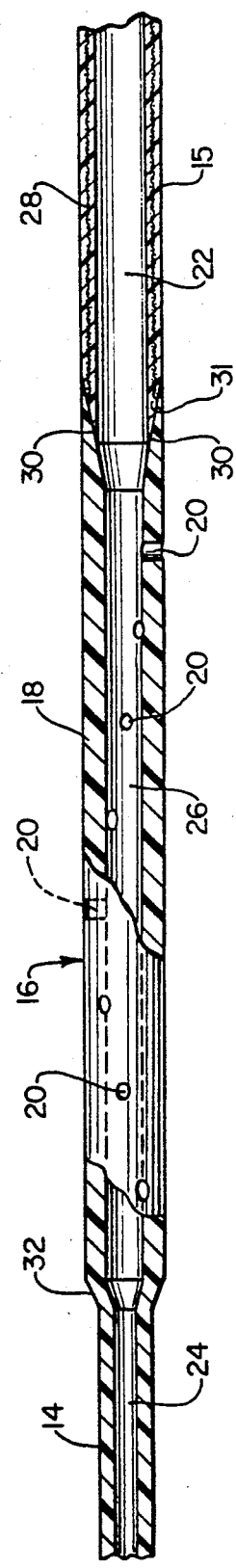
FIG. 2 is an enlarged, plan view, with portions taken in longitudinal section, of a segment of the catheter of FIG. 1.

Referring to the drawings, angiographic catheter 10 is generally of the design of present, commercially available angiographic catheters except for the differences described herein. Catheter 10 may typically be made of any appropriate flexible plastic material such as polyurethane, for example, defining a proximal hub 12 of conventional design, a flexible, tubular body 15, and a distal pigtail tip 14, which also may be generally conventional except as otherwise indicated herein.

Flexible, tubular body 15 carries on its distal end, by heat sealing a tubular tip 16. Tip 16, in turn, defines an intermediate portion 18, which defines a typically generally spiral array of side holes 20. At the distal end of intermediate portion 18 is the pigtail tip section 14.

Tubular body 15 defines a first bore portion 22; pigtail section 14 defines second bore portion 24; and intermediate section 18 defines intermediate or third bore portion 26. Tubular body 15 also carries a conventional braided metal fiber reinforcing sleeve 28 which terminates at the frustoconical junction area 30 between tubular body 15 and intermediate portion 18.

In accordance with this invention, a first "step-down" in the bore diameter is provided at junction 30, which, as shown, is a conical section seal between tubular body 15 and intermediate portion 18, and which may be formed in a conventional catheter fusing die for heat sealing members 15 and 18 together. The catheter outer diameter is constant between members 15 and 18. Hence, because of the increase in the wall thickness of intermediate portion 18, compared with the wall thickness of tubular body 15, heat fusion sealing processes can take place with a significantly increased likelihood that the distal end 31 of braided wire sheath 28 will be buried, because of the availability of more plastic material due to the increased wall thickness of intermediate portion 18. This first "step-down" section 30 provides such a manufacturing advantage. Additionally, the thickened wall of intermediate section 18 provides increased resistance to unplanned collapsing or buckling of that section of the catheter without any increase in the outer diameter thereof, to obtain desired clinical benefits as described above.

A second "step-down" bore section 32 of catheter 10 occurs at the distal end of intermediate section 18, where pigtail section 14 is integrally attached. This second step-down 32 causes bore 24 of pigtail section 14 to be of less diameter than bore 26 of intermediate section 18. The effect of this, as stated before, is to direct a greater percentage of fluid flow through the catheter laterally outwardly through apertures 20 rather than longitudinally through bore 24. The diameters and arrangements of the respective bores 24, 26, and ports 20 can be adjusted so that the ratio of lateral to longitudinal flow can be exactly that which is clinically desired for the specific purpose.

The catheter of this invention may have, for example, a French 6 tip. The diameter of bore 22 of tubular body 15 may be about 0.051 inch, while the diameter of third bore 26 in the intermediate section 18 may be about 0.048 inch. The diameter of second bore 24 in the pigtail 14 may then be about 0.042 inch. The outer diameter of sections 15 and 18 of the catheter may be about 0.08 inch, while the outer diameter of pigtail tip 14 may be about 0.07 inch. These dimensions are provided for merely exemplary purposes, and may vary in accordance with the desired French size of the catheter and for other reasons. The length of catheter 10 may typically correspond to conventional catheters for angiography.

The above has been offered for illustrative purposes only, and is not intended to limit the scope of the invention of this application, which is as defined in the claims below.

That which is claimed is:

1. A catheter which defines a flexible, tubular body and a tubular tip carried at the distal end of said body, at least the majority of said tubular body defining a first bore portion having a first diameter; said catheter defining side holes adjacent said distal end, said catheter defining a second bore portion distal to essentially all of said side holes present and having a second diameter which is less than the first diameter; said catheter also defining an intermediate, tubular portion between the first and second bore portions, said intermediate portion having a third bore diameter that is less than the first diameter and greater than the second diameter, said intermediate portion defining a thicker catheter wall than the catheter wall defining the first bore portion.

2. The catheter of claim 1 in which said flexible, tubular body is joined to said tubular tip at a junction area between the first bore portion and the intermediate portion.

3. The catheter of claim 1 in which said side holes are defined in the intermediate portion.

4. The catheter of claim 1 which defines stepped, bore-reducing areas between (1) the first bore portion and the intermediate portion and (2) the intermediate portion and the second bore portion.

5. The catheter of claim 1 in which said tubular body carries a tubular reinforcing sleeve made of metal strands.

6. A catheter which defines a flexible, tubular body and a tubular tip carried at the distal end of said body, at least the majority of said tubular body defining a first bore portion having a first diameter, said tubular body carrying a tubular reinforcing sleeve made of metal strands embedded in the wall of said tubular body, said catheter defining a tubular, intermediate portion distal to said tubular body, said tubular intermediate portion having side holes, said catheter defining a second bore portion distal to said intermediate portion and side holes, said second bore portion having a second diameter which is less than the first diameter, the second bore portion comprising a pigtail tip, the bore of said catheter extending through the distal end thereof, said intermediate tubular portion having a third bore diameter that is less than the first diameter and greater than the second diameter, said intermediate portion defining a thicker catheter wall than the catheter wall defining said first bore portion, said flexible tubular body being joined to the tubular tip at a junction area between the first bore portion and the intermediate portion.

7. The catheter of claim 6 which defines stepped, bore-reducing areas between (1) the first bore portion and the intermediate portion and (2) the intermediate portion and the second bore portion.

8. A catheter which defines a flexible, tubular body and a tubular tip carried at the distal end of said body, at least the majority of said tubular body defining a first bore portion having a first diameter; said catheter defining side holes adjacent said distal end, said catheter defining a second bore portion distal to said side holes having a second diameter which is less than the first diameter, the catheter part defining the second bore portion comprising a pigtail tip, the bore of said catheter extending through the distal end thereof; said catheter also defining an intermediate tubular portion between the first and second bore portions, said intermediate portion having a third bore diameter that is less than the first diameter and greater than the second diameter, said intermediate portion defining a thicker catheter wall than the catheter wall defining the first bore portion.

9. The catheter of claim 8 in which said flexible, tubular body is joined to said tubular tip at a junction area between the first bore portion and the intermediate portion.

10. The catheter of claim 9 in which said side holes are defined in the intermediate portion.

11. The catheter of claim 10 which defines stepped, bore-reducing areas between (1) the first bore portion and the intermediate portion and (2) the intermediate portion and the second bore portion.

12. The catheter of claim 11 in which said tubular body carrier a tubular reinforcing sleeve of metal strands.

13. The catheter of claim 8 which defines stepped, bore-reducing areas between (1) the first bore portion and the intermediate portion and (2) the intermediate portion and the second bore portion.

14. The catheter of claim 8 in which said side holes are defined in the intermediate portion.

15. The catheter of claim 8 in which said tubular body carries a tubular reinforcing sleeve of metal strands.

* * * * *

UNITED STATES PATENT AND TRADEMARK OFFICE
CERTIFICATE OF CORRECTION

PATENT NO. : 5,069,673
DATED : Dec. 3, 1991
INVENTOR(S) : Jacqueline A. Shwab

It is certified that error appears in the above-identified patent and that said Letters Patent is hereby corrected as shown below:

On the title page: Item

[22] Filed: Feb. 7, 1990

Signed and Sealed this

Thirtieth Day of March, 1993

*Attest:*

STEPHEN G. KUNIN

*Attesting Officer*      *Acting Commissioner of Patents and Trademarks*